United States Patent [19]

Gibert et al.

[11] 4,041,768

[45] Aug. 16, 1977

[54] DEVICE FOR MEASURING THE MASS OF PARTICLES OF AN AEROSOL PER VOLUME UNIT

[75] Inventors: Alain Gibert, Gan; Roger Camps, Jurancon, both of France

[73] Assignee: Societe Nationale des Petroles D'Aquitaine, Courbevoie, France

[21] Appl. No.: 647,066

[22] Filed: Jan. 7, 1976

[30] Foreign Application Priority Data

Jan. 15, 1975 France .................... 75.01128

[51] Int. Cl.² ............... G01N 15/06; B03C 3/00
[52] U.S. Cl. ................................ 73/28; 55/152
[58] Field of Search ............ 73/28, 23; 324/71 CP, 324/32; 55/152, 270

[56] References Cited

U.S. PATENT DOCUMENTS

| | | | |
|---|---|---|---|
| 3,114,877 | 12/1963 | Dunham | 324/71 CP |
| 3,449,667 | 6/1969 | Gourdine | 324/71 CP |
| 3,561,253 | 2/1971 | Dorman | 73/28 |
| 3,582,711 | 6/1971 | Jahnke | 55/152 |
| 3,653,253 | 4/1972 | Olin | 73/28 |
| 3,679,973 | 7/1972 | Smith | 73/28 |
| 3,715,911 | 2/1973 | Chuan | 73/28 |
| 3,879,986 | 4/1975 | Sehmel | 73/28 |

Primary Examiner—Richard C. Queisser
Assistant Examiner—Stephen A. Kreitman
Attorney, Agent, or Firm—Burgess, Ryan and Wayne

[57] ABSTRACT

The present invention is related to a device for measuring the mass of particles of an aerosol per volume unit. It comprises a solid measuring body, measuring means for measuring the resonance frequency of said solid measuring body, means for generating a flow of air loaded with particles and for directing said air flow toward a planar receiving electrode and means for electrically loading said particles with a polarity opposed to that of the planar receiving electrode.

3 Claims, 7 Drawing Figures

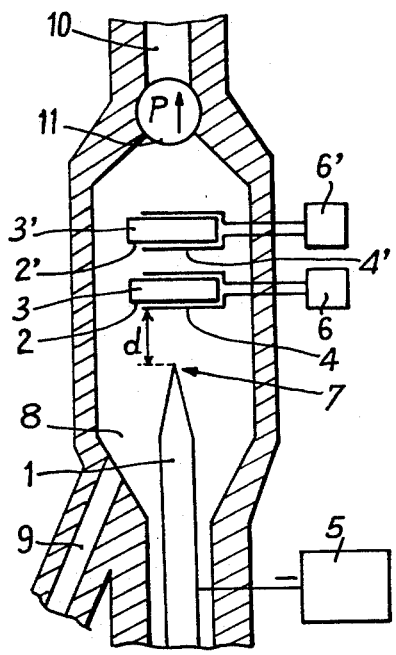
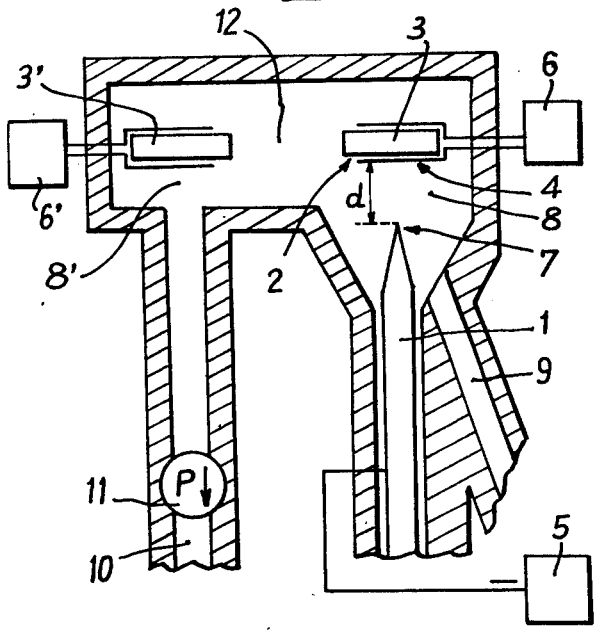
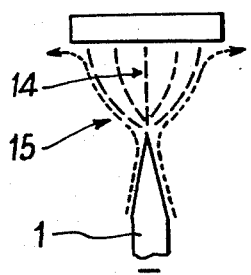
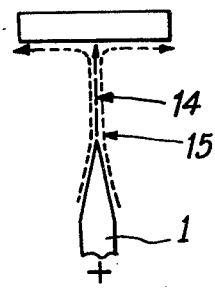
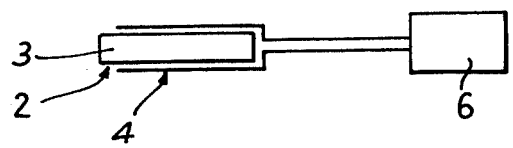
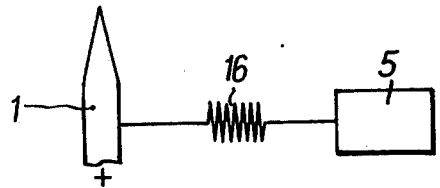

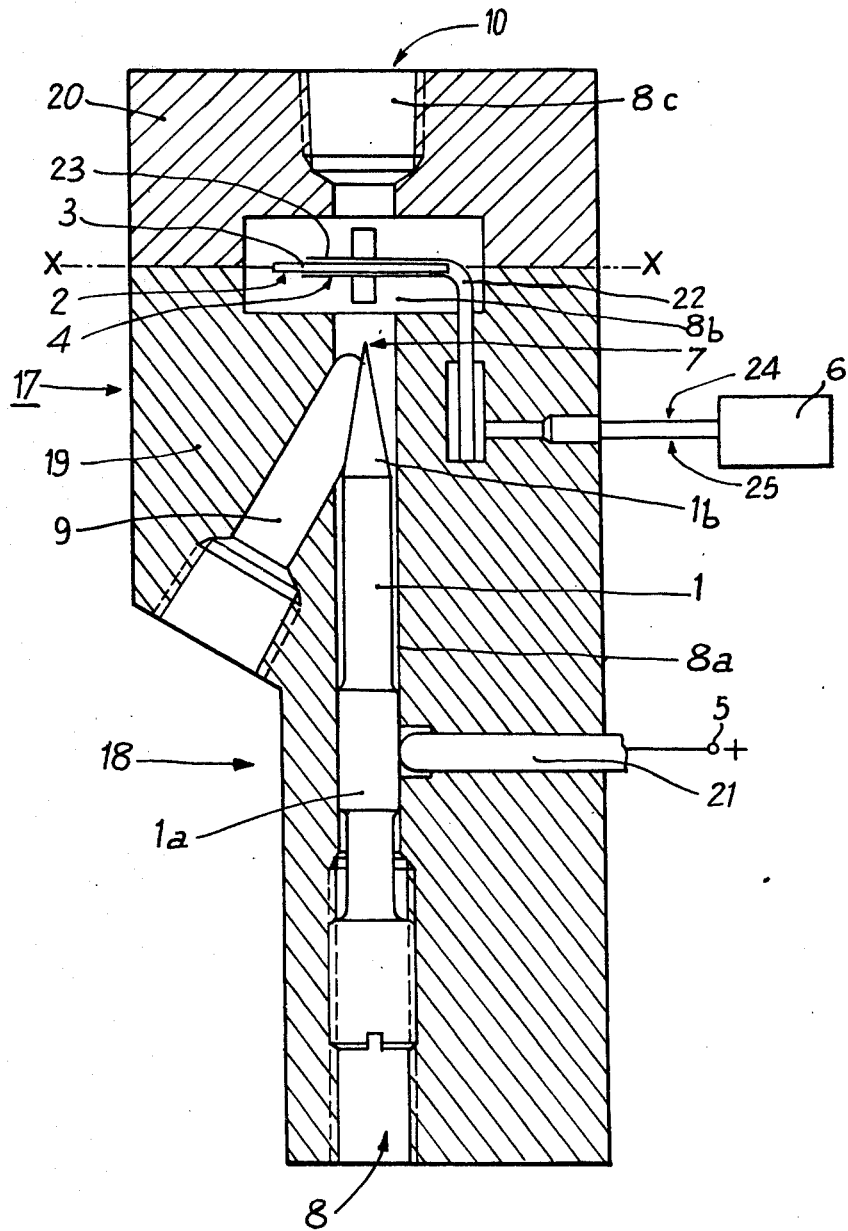

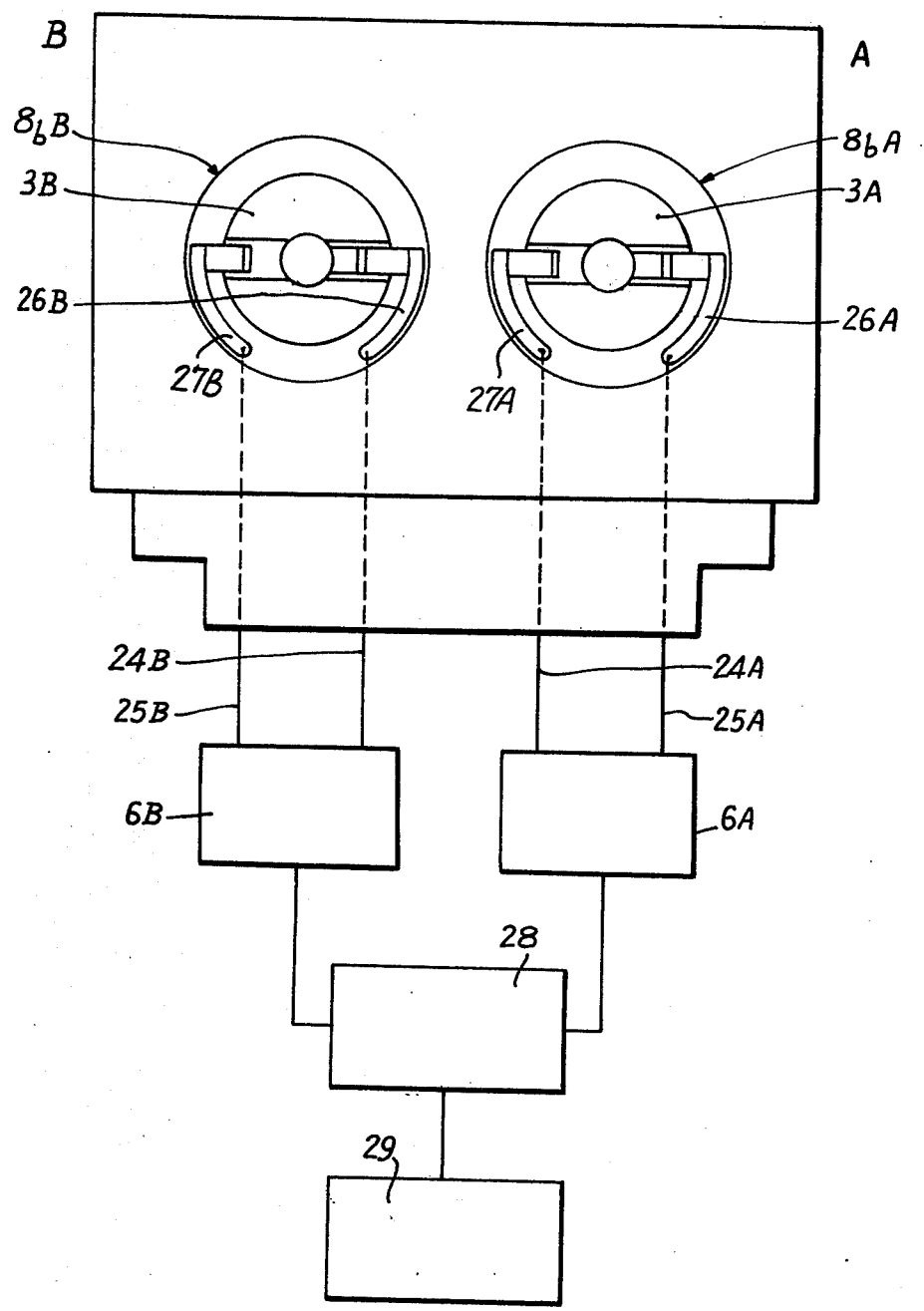

DEVICE FOR MEASURING THE MASS OF PARTICLES OF AN AEROSOL PER VOLUME UNIT

The present invention is related to a device for measuring the mass of particles of an aerosol per volume unit.

Various devices are known which make use of the fact that certain substances have the property of presenting predetermined resonance frequency for a given geometric configuration, said resonance frequency being bound to vary when the configuration is modified, especially under the effect of a deposit of particles. In these known devices the deposit of moving aerosol particles on a planar surface of a body, called measuring body, is caused by the passage of a high voltage electric current between a metallic point and the planar surface of the measuring body, said surface being perpendicular to the axis of the aforementioned point and being partially covered by a planar receiving electrode. The end of the point is separated from the planar surface by a distance greater than the spark length in the atmosphere. In these devices the resonance frequency of the measuring body is compared to the resonance frequency of a reference body maintained in similar temperature and pressure conditions and on the surface of which no deposit is formed.

In the various types of known devices, the reference body is placed in the path of the flow of particle containing air, and there is a risk of formation of a residual deposit which may modify the configuration of the reference body. Furthermore, the air flow is initiated by a suction pump which is generally arranged at the end of the circuit; the output rate of such an installation may undergo the influence of variations which are independent from the rate of precipitation of the particles.

In these same devices the metallic point is connected to the negative terminal of a high voltage electric current generator and the planar receiving electrode is connected to measuring means adapted to measure the resonance frequency of the measuring body. On account of this arrangement, fractions of material are detached from the point, which results in modifying the configuration of the latter. These modifications of the configuration of the point result, in turn, in modifications of the intensity of the dispensed current, these latter modifications causing generally the efficiency of particle precipitaion on the planar surface of the measuring body to decrease. Nothing can prevent these current intensity variations from occurring, since the high voltage current sources are voltage-controlled, but not intensity-controlled.

The instant invention allows these drawbacks to be overcome. By connecting the point to the positive terminal, the induced air flow, which is also called "electrical air flow" or "electrical wind" and which may occur in the known devices becomes sufficiently powerful so that it is no longer necessary to rely on the action of a suction pump, especially when taking into account the fact that the passage through which flows the air loaded with aerosol particles has been designed in such a manner that the pressure losses are reduced to a minimum.

When the point is connected to the positive terminal of the high voltage generator, the configuration of said point changes very slowly, and thus the resulting current variations are minimized. Nevertheless, with a view to obtain a still more constant deposit formation efficiency, it is advantageous to provide a current intensity control or regulation of the feeding current.

A device for measuring the mass of the particles of an aerosol per volume unit comprises:

- a solid body, or measuring body, having a resonance frequency and comprising a planar surface partially covered by a planar particle receiving electrode, said resonance frequency being a function of the mass of the deposited particles;

- measuring means for measuring the resonance frequency of said solid measuring body, especially as compared to the resonance frequency of a second solid body, or reference body, having the same characteristics as said measuring body and being maintained in the same temperature and pressure conditions as said measuring body;

- means for generating a flow of air loaded with particles and for directing said air flow toward said planar receiving electrode; and

- means for electrically loading said particles with a polarity opposed to that of the planar receiving electrode.

In the device according to the invention the means for generating a flow of air loaded with particles and for directing said air flow toward the planar receiving electrode, as well as the means for electrically loading said particles with a polarity opposite to that of said planar receiving electrode are constituted by a metallic point the geometrical axis of which is perpendicular to said planar receiving electrode, and which is separated from said planar receiving electrode by a distance of about 3 to 15 mm, said point being connected to the positive terminal of a source of electric current delivering a direct current of very high voltage, whereas said planar receiving electrode is connected to measuring means adapted to measure the resonance frequency of said measuring body, said point and said measuring body being arranged within a measuring conduit coaxial to said point, said measuring conduit comprising an air inlet nozzle opening near the end of said point, an axial aperture opening into the atmosphere being provided at a location opposite said point, and the assembly of said measuring body, said point and said measuring conduit constituting a measuring cell.

The solid reference body may be arranged in a space called reference space which is entirely closed, and which may be constituted by a conduit similar to the measuring conduit or by a conduit having the same characteristics as those of said measuring conduit, the air inlet nozzle and the axial aperture being closed in these various embodiments.

When the reference space is constituted by a cell having the same characteristics as those of the measuring cell the air inlet nozzle and the axial aperture of which are closed, it is possible, too, to use alternatively each one of said cells as a measuring cell or as a reference cell. Due to this possibility the instant device presents a considerable flexibility of use and optimum control and calibrating capacities.

In a preferred embodiment the direct current source is provided, for each cell, with current intensity control means regulating the delivered current, said control means comprising more particularly means for maintaining said current intensity at a constant value. Convenient control means of this kind which may be used to this end are disclosed in U.S. Patent Application Ser.

No. 647,086 filed by the Applicant, herein on Jan. 7, 1976.

The invention will be more clearly understood in the light of the description herein below with reference to the appended drawings which show an embodiment of the invention by way of illustration, but not of limitation.

FIG. 1 shows a known device comprising a reference body arranged downstream of the measuring body.

FIG. 2 shows another known device comprising a reference body arranged upstream of the measuring body.

FIG. 3 represents the corona effect obtained when using a point to which a negative load is applied.

FIG. 4 represents the corona effect when using a point to which a positive load is applied.

FIG. 5 shows means for controlling the corona effect by using a resistor.

FIG. 6 is a longitudinal section of the measuring cell.

FIG. 7 is a transverse section of the measuring and reference cells.

FIGS. 1 and 2 schematically show two known devices for measuring the mass of the particles of an aerosol per volume unit. According to each one of these Figures, a metallic point 1 is arranged with its axis perpendicular to a planar surface 2 of a measuring body 3. The surface 2 is partially covered by a planar receiving electrode 4. The measuring body 3 has a resonance frequency which varies as the configuration of body 3 varies, especially due to the formation of a deposit of particles on planar electrode 4.

Point 1 is connected to a negative terminal of a very high voltage current source 5. Planar electrode 4 is connected to means for measuring the resonance frequency of measuring body 3, said means being constituted e.g. by an oscillator 6.

The end 7 of point 1 is located at a distance $d$ from the planar electrode 4, said distance $d$ being greater than the sparking distance in the air for the high voltage current used in the device.

FIG. 1 shows an embodiment in which point 1 and measuring body 3 are arranged in a coaxial measuring conduit 8. Conduit 8 comprises an air inlet nozzle 9 opening near the end 7 of point 1, as well as an aperture 10 opening into the atmosphere, which is associated with a metering pump 11.

FIG. 2 shows a similar arrangement wherein the end 7 of point 1 is located at a distance $d$ from planar electrode 4 which partially covers the planar surface 2 of the measuring body 3. However in this embodiment the reference body 3' is arranged in a reference conduit 8' constituting the lateral prolongation of the measuring conduit 8 and communicating with the latter by a passage 12.

In the devices according to FIGS. 1 and 2, point 1 is connected to the negative terminal of an electric current source 5 delivering a current of very high voltage, the receiving elecrode 4 covering a portion of the planar surface 2 of measuring body 3 being connected to oscillator 6. A receiving electrode 4' covering a portion of planar surface 2' of reference body 3' is connected to an oscillator 6'.

The following comments may be made with respect to these two devices: 1. The reference body, which is arranged downstream of the measuring body, with reference to the direction of the air flow, receives aerosol particles which could not settle on the measuring body, or aerosol particles which have eventually been detached from the measuring body.

2. On account of the fact that the point 7 has a negative potential, said point is rapidly deteriorated; this deterioration which may be easily observed results in an increase of the radius of curvature of said point. The variation of the electric current intensity between the point and the electrode generally result in a progressive decrease of the efficiency of particle depositing on the electrode.

3. FIG. 3 schematically shows the distribution of the lines of current 14, called "corona effect", between a point 1 having a negative potential and a planar electrode orthogonal with respect to the axis of said point. These lines of current 14 which are represented by dashed lines, define a volume of tapered configuration, and the air surrounding the point is carried, in the form of air jets 15 represented by pointed lines, along the flow path. The air contacts the electrode in the immediate vicinity of the median zone of the latter, and then diverges toward the periphery. In this device, the aerosol particles are able to deposit in a regular manner on the median portion of the planar receiving electrode.

The attempt to obtain an optimum distribution of the particles on the sensitive electrode of the measuring body has led to designing the device according to FIG. 4, wherein the lines of current 14 are arranged as shown by the dashed lines, as shown in FIG. 3. It should be noted that in this case the "electric wind" becomes sufficient to ensure an output flow rate of about one litre per minute. It is thus no longer necessary to operate a suction pump at the outlet of the measuring cell.

With a view to obtaining a regular air flow the intensity of the electric current corresponding to the corona effect must be stabilized; this stabilization is achieved by two means. In the first place, as shown in FIG. 5, a resistor 16 of about 10 megohms connected in series with the feeding conductor of the point attenuates the intensity variations having very short periods. Furthermore, a device such as the intensity stabiliser for very high voltage current disclosed in the aforementioned U.S. Patent Application Ser. No. 647,086 maintains the current intensity at a predetermined value and avoids any deviations therefrom.

FIG. 6 is a longitudinal section showing a measuring cell A or a reference cell B of a device according to the invention for measuring the mass of particles of an aerosol per volume unit.

A block 17 made of plastic material having a high resistivity and a high dielectric coefficient, e.g. the material sold under the commercial designation "ALTUGLAS" is provided with a measuring conduit 8 of cylindrical cross-section. This measuring conduit comprises a plurality of coaxial sections, to wit: a section **8*a* having a small diameter as compared to its length and wherein a metallic point 1 is fixed, a section 8*b* having a comparatively great diameter with respect to its length and which constitutes a discharge chamber wherein the measuring body 3 is arranged, said measuring body being constituted by a piezo-electric quartz blade perpendicular to the axis of conduit 8, and a section 8*c* the diameter of which is approximately equal to that of section 8*a* and which opens into the atmosphere through an aperture 10.**

Point 1 comprises a plurality of cylindrical sections at least one of which (**1*a*) has a diameter equal to that of section 8*a* of conduit 8, and a frusto-conical terminal section 1*b*** made of tungsten steel or of stainless steel, the end of said frusto-conical section being preferentially made of tungsten.

Block 17 is a parallelepiped body on which a prismatic relief portion 18 is provided with a view to facilitating the provision of an air inlet nozzle 9 opening into section 8a near the conical end 7 of point 1b.

With a view to facilitating the assembly and the dismounting of the measuring or reference cell, block 17 is divided into two portions 19 and 20 defined by a plane indicated at x–x and constituted in the embodiment according to FIG. 6 by the center plane of the discharge chamber 8b. Once assembled, parts 19 and 20 are maintained in their relative position by means of screws (not shown).

Point 1 is connected to a positive terminal of a high-voltage current source 5 by means of a conductor 21 extending through body 19 and maintained in contact with point 1 on a cylindrical section of the latter.

Measuring body 3 is maintained in the center zone of discharge chamber 8b by means of a supporting element 22. Measuring body 3 comprises a planar surface 2 located in front of the point and that planar surface 2 supports on a portion of its area, especially the center portion thereof, a planar particle receiving electrode 4. Said planar electrode 4 as well as an electrode 23 applied to the opposite surface are connected by conductors 24 and 25 to an oscillator 6.

FIG. 7 is a sectional view taken in plane x–x of an assembly constituted by a measuring cell A and a reference cell B mounted in the vicinity of said measuring cell. This figure shows the sectional form of the discharge chamber 8bA of measuring cell A, which contains a piezo-electric quartz blade 3A having a circular periphery, and the section 8bB of reference cell B containing a quartz disc or blade 3B which also has a circular periphery.

On each measuring body 3A, 3B, and in front of the points 1A, 1B, electrically conductive connecting pieces 26A,/26B, 27A and 27B, respectively, each forming substantially a segment as shown, are mounted in a position coaxial with respect to the corresponding measuring body 3A, 3B. Connecting pieces 27A and 27B are each coaxial with the corresponding measuring body 3A and 3B and are mounted on the respective faces thereof which are located in front of points 1A and 1B, respectively. Said connecting pieces 26A, 26B, 27A, 27B are each connected to a corresponding circular electrode, and are also connected, respectively, by conductors 25A, 24B, 24A, 25B to oscillators 6A and 6B of cells A and B respectively, by corresponding conductors 25A, 24B, 24A and 25B.

The output terminals of oscillators 6A and 6B are connected to a frequency mixer 28 the outlet of which is connected to a frequency meter 29 comprising an indicating scale or recording means for indicating or recording the difference between the resonance frequencies of bodies 3A and 3B, respectively.

In one embodiment of the device according to the invention for measuring the mass of particles of an aerosol per volume unit, wherein the point is connected to the positive terminal of source of +10,000 Volts, D.C., the planar receving electrode of the measuring body being connected to the positive terminal of said source said point being arranged at a distance $d$ of 15 mm from the measuring electrode, the air flow rate due to the "electric wind" amounts to 1 liter of air per min.

The sizes of the captured aerosol particles are typically in the range of 0.01 to 50 microns.

The operations of comparison of the resonance frequencies of the measuring body and the resonance frequencies of the reference body are effected in a continuous manner, or stepwise in accordance with a selected timing sequence.

The indications obtained are accurate with a tolerance on the order of one Hertz.

The embodiment described hereinabove, which has yielded the above-mentioned results is disclosed by way of illustration, but not of limitation.

What is claimed is:

1. A device for measuring the mass of particles contained in an aerosl per volume unit thereof, comprising:
   a block of electrical insulating material having a measuring cell and a reference cell defined therein;
   each said cell comprising a measuring conduit, an inlet conduit communicating with said measuring conduit for introducing a flow of air loaded with particles into said measuring conduit, and an outlet conduit communicating with said measuring conduit at one end and with the atmosphere at the other end;
   a pointed charging electrode disposed in each of said measuring conduits opposite each of the corresponding outlet conduits, the pointed end of each of said pointed electrodes being disposed adjacent the junction of said inlet conduit and said measuring conduit and oriented at an acute angle to said inlet conduit so that said inlet conduit directs said particle-loaded air stream toward said pointed end;
   a vibratory element comprising a circular piezoelectric quartz disc disposed in each of said cells, each of said elements having a pre-determined resonance frequency, the vibratory element within said measuring cell having a circular planar measuring particle receiving electrode facing the corresponding pointed electrode and disposed a predetermined distance therefrom, the vibratory element disposed within said reference cell having a circular planar reference electrode disposed thereon facing the corresponding pointed electrode and disposed a predetermined distance therefrom, the plane of each of said electrodes being substantially normal to the direction of orientation of the corresponding pointed electrode, the distance between each pointed electrode and the corresponding planar electrode being greater than that required to generate a spark therebetween when a predetermined high voltage is applied between each of said pointed an a planar electrodes;
   means for maintaining the current flowing between the electrodes of said measuring cell at a desired value;
   each of said vibratory elements being disposed within the corresponding cell in such a manner that air may flow around all sides thereof between said inlet and outlet conduits;
   means for suspending each of said vibratory elements within the corresponding cell thereof in such a manner that the resonance frequency of each element varies with its mass;
   means for measuring the resonance frequency of each of said vibratory elements and generating an output signal corresponding to the difference therebetween;
   the arrangement of each of said cells and the corresponding conduits being such that the surface of each vibratory member opposite the corresponding planar electrode faces the corresponding outlet conduit, and the distance between the point of each pointed electrode and the nearest point on the surface of the corresponding planar electrode is on the order of 15 mm.; and means for establishing and maintaining a high voltage DC potential difference between (i) the pointed electrode and planar electrode of said measuring cell and (ii) the pointed electrode and planar electrode of said reference cell, the potential of each of said pointed electrodes being positive with respect to the corresponding planar electrode;

the voltage applied between the pointed and planar electrodes of said measuring cell being on the order of 10,000 volts to cause the flow of particle-containing air through said measuring cell by the effect of an electric wind, the geometry of said measuring cell as set forth above being such that said cell presents minimal impedance to said flow.

2. A device for measuring the mass or particles contained in an aerosol per volume unit thereof, which aerosol is caused to flow through said device, comprising a block of electrically insulating material, a measuring cell and a reference cell defined within said block, a planar measuring receiving electrode arranged within said measuring cell and a planar reference electrode arranged within said reference cell, said two cells being juxtaposed with respect to each other, each one of said electrodes being disposed adjacent a pointed electrode disposed perpendicularly to the associated receiving electrode and connected to the positive pole of a high voltage source producing a voltage of substantially 10,000 volts, said source including a current regulator for maintaining the current delivered by said source at a constant value, a resistor connected in series between each of said pointed electrodes and said current source, the pointed end of each pointed electrode being directed towards one surface of the associated receiving electrode and located at a distance therefrom which is longer than the spark gap corresponding to said voltage, an inlet nozzle for directing a stream of said aerosol toward the pointed end of said pointed electrode associated with said receiving electrode in said measuring cell, and an outlet passage opening into said measuring cell at a location facing the other surface of the associated receiving electrode of said measuring cell, first and second oscillators connected to respective ones of said receiving electrodes, the respective output terminals of said oscillators being connected to a frequency mixer which is connected, in turn, by its output terminals to a frequency meter adapted to display and/or record the difference between the respective resonance frequencies of said two cells, said aerosol being caused to flow through said device by the effect of an electric wind due to the high voltage positive polarity of said pointed electrode of said measuring cell.

3. A device according to claim 1, wherein each receiving electrode comprises a piezo-electric quartz disc having a circular periphery and provided on both sides thereof with substantially circular electrode elements made of electrically conductive material and connected to the associated oscillator.

* * * * *

UNITED STATES PATENT OFFICE
CERTIFICATE OF CORRECTION

Patent No. 4,041,768      Dated   August 16, 1977

Inventor(s)   Alain Gibert, et al

It is certified that error appears in the above-identified patent and that said Letters Patent are hereby corrected as shown below:

Column 4, line 38:  After "point" insert --1--.

lines 51 & 52:  After '"ALTUGLAS"' insert a comma.

Column 5, line 3:  "parallelepiped" should be --parallelepiped-shaped--.

line 61:  After "of" insert --a--.

Column 6, line 50:  "an a" should be --and--.

Signed and Sealed this

*Twelfth* Day of *February 1980*

[SEAL]

*Attest:*

SIDNEY A. DIAMOND

*Attesting Officer*   *Commissioner of Patents and Trademarks*